United States Patent
Rahaman et al.

(10) Patent No.: US 8,641,774 B2
(45) Date of Patent: Feb. 4, 2014

(54) SYNTHETIC OSTEOCHONDRAL COMPOSITE AND METHOD OF FABRICATION THEREOF

(75) Inventors: Mohamed Naushad Rahaman, Rolla, MO (US); Bhajanjit Singh Bal, Columbia, MO (US)

(73) Assignee: The Curators of the University of Missouri, Carbondale, IL (US)

( * ) Notice: Subject to any disclaimer, the term of this patent is extended or adjusted under 35 U.S.C. 154(b) by 1078 days.

(21) Appl. No.: 12/209,943

(22) Filed: Sep. 12, 2008

(65) Prior Publication Data

US 2009/0076624 A1 Mar. 19, 2009

Related U.S. Application Data

(60) Provisional application No. 60/993,784, filed on Sep. 14, 2007.

(51) Int. Cl.
*A61F 2/02* (2006.01)

(52) U.S. Cl.
USPC .................................... 623/23.72

(58) Field of Classification Search
USPC .......... 623/23.72, 23.75, 23.63; 424/424–426
See application file for complete search history.

(56) References Cited

U.S. PATENT DOCUMENTS

| | | | |
|---|---|---|---|
| 6,306,424 B1 * | 10/2001 | Vyakarnam et al. | 424/426 |
| 6,333,029 B1 | 12/2001 | Vyakarnam et al. | |
| 2003/0204238 A1 * | 10/2003 | Tedeschi | 623/1.11 |
| 2003/0216669 A1 | 11/2003 | Lang et al. | |
| 2005/0069572 A1 * | 3/2005 | Williams et al. | 424/426 |
| 2005/0169959 A1 | 8/2005 | Hunter et al. | |
| 2006/0188940 A1 * | 8/2006 | Cima et al. | 435/7.1 |
| 2006/0233855 A1 | 10/2006 | Seliktar et al. | |
| 2007/0014867 A1 | 1/2007 | Kusanagi et al. | |

OTHER PUBLICATIONS

International Search Report and Written Opinion dated Nov. 21, 2008 for PCT/US2008/076411 (10 pages).
Hjelle et al., Articular cartilage defects in 1,000 knee arthroscopies. Arthroscopy. Sep 2002; 18(7):730-734.
Buckwalter JA., Articular cartilage injuries. Clinical Orthopaedics & Related Research, Sep. 2002(402):21-37.
Rahaman et al., Stem cell-based composite tissue constructs for regenerative medicine. Biotechnology & Bioengineering, Aug. 5, 2005;91(3):261-284.
Vacanti JP, Langer R., Tissue engineering: the design and fabrication of living replacement devices for surgical reconstruction and transplantation. Lancet. 1999;354, Suppl 1:SI32-34.
Chang C-H, et al. Tissue engineering-based cartilage repair with allogenous chondrocytes and gelatin-chondroitin-hyaluronan tri-copolymer scaffold: A porcine model assessed at 18, 24, and 36 weeks. Biomaterials. Mar. 2006;27 (9):1876-1888.
Gao J. Repair of osteochondral defect with tissue-engineered two-phase composite material of injectable calcium phosphate and hyaluronan sponge. Tissue Engineering. 2002;8(5):827-837.

(Continued)

*Primary Examiner* — Gregory Anderson
(74) *Attorney, Agent, or Firm* — Polsinelli PC (57) ABSTRACT

An osteochondral composite including a hydrogel with implanted biological cells joined to a porous supportive base at a mechanically-interlocked interface is disclosed. A method of fabricating the osteochondral composite and a method of treating damaged or diseased articular cartilage by implanting an osteochondral composite are also disclosed.

41 Claims, 8 Drawing Sheets

(56) References Cited

OTHER PUBLICATIONS

Gao J, et al. Tissue-engineered fabrication of an osteochondral composite graft using rat bone marrow derived mesenchymal stem cells. Tissue Engineering. Aug. 2001;7(4):363-371.

Song H-X. Repairing articular cartilage defects with tissue-engineering cartilage in rabbits. Chinese Journal of Traumatology (English Edition). 2006;9(5):266-271.

Schaefer et al. Tissue-engineered composites for the repair of large osteochondral defects. Arthritis & Rheumatism. Sep. 2002;46(9):2524-2534.

Guo X, et al. Repair of osteochondral defects with autologous chondrocytes seeded onto bioceramic scaffold in sheep. Tissue Engineering. Nov.-Dec. 2004; 10(11-12): 1830-1840.

Masuoka K. Tissue engineering of articular cartilage with autologous cultured adipose tissue-derived stromal cells using atelocollagen honeycomb-shaped scaffold with a membrane sealing in rabbits. Journal of Biomedical Materials Research Part B: Applied Biomaterials. 2006,79(1):25-34.

Pittenger MF, et al. Multilineage potential of adult human mesenchymal stem cells. Science. Apr. 2, 1999;284(5411): 143-147.

Mackay AM, et al., Chondrogenic differentiation of cultured human mesenchymal stem cells from marrow. Tissue Engineering 1998;4(4):415-428.

Drury JL, et al. Hydrogels for tissue engineering: scaffold design variables and applications. Biomaterials. Nov. 2003;24 (24):4337-4351.

Elisseeff et al., Photoencapsulation of chondrocytes in poly(ethylene oxide)-based semi-interpenetrating networks. Journal of Biomedical Materials Research. Aug. 2000;51(2): 164-171.

Wang DA, et al. Synthesis and characterization of a novel degradable phosphate-containing hydrogel. Biomaterials. Oct. 2003;24(22):3969-3980.

Kawcak CE, et al. The role of subchondral bone in joint disease: a review. Equine Veterinary Journal. Mar. 2001;33(2): 120-126.

Tanaka T. Use of a biphasic graft constructed with chondrocytes overlying a betatricalcium phosphate block in the treatment of rabbit osteochondral defects. Tissue Engineering. 2005;11(1-2):331-339.

Awad HA, et al., Autologous mesenchymal stem cell-mediated repair of tendon. Tissue Engineering. Jun. 1999;5 (3):267-277.

Alhadlaq A, et al. Tissue-engineered neogenesis of human-shaped mandibular condyle from rat mesenchymal stem cells. Journal of Dental Research. Dec. 2003;82(12):951-956.

Brink M, et al. A. Compositional dependence of bioactivity of glasses in the system, Biomedical Materials Research. Oct. 1997;37(1): 114-121.

Fu Q, et al. Preparation and bioactive characteristics of a porous 13-93 glass, and fabrication into the articulating surface of a proximal tibia. Journal of Biomedical Materials Research Part A. Jul. 2007;82(1):222-229.

Levine BR, et al., Experimental and clinical performance of porous tantalum in orthopedic surgery. Biomaterials.. Sep. 2006;27(27):4671-4681.

Chu TM, et al. Manufacturing and characterization of 3-d hydroxyapatite bone tissue engineering scaffolds. Annals of the New York Academy of Sciences. Jun. 2002;961:114-117.

Hollister SJ, et al. Optimal design and fabrication of scaffolds to mimic tissue properties and satisfy biological constraints. Biomaterials. Oct. 2002;23(20):4095-4103.

Sherwood JK, et al. A three-dimensional osteochondral composite scaffold for articular cartilage repair. Biomaterials. Dec. 2002;23(24):4739-4751.

Solchaga LA, et al. Hyaluronan-based polymers in the treatment of osteochondral defects. Journal of Orthopaedic Research. Sep. 2000; 18(5):773-780.

Grande DA, al. et al. Evaluation of matrix scaffolds for tissue engineering of articular cartilage grafts. Journal of Biomedical Materials Research. Feb. 1997;34(2):211-220.

Niederauer CG, et al. Evaluation of multiphase implants for repair of focal osteochondral defects in goats. Biomaterials. Dec. 2000;21 (24):2561-2574.

van Susante JL, et al. Chondrocyte-seeded hydroxyapatite for repair of large articular cartilage defects. A pilot study in the goat. Biomaterials. Dec. 1998; 19(24):2367-2374.

Lee KY, et al. Hydrogels for tissue engineering. Chemical Reviews. Jul. 2001; 101 (7): 1869-1879.

Pelker RR, et al. Biomechanical properties of bone allografts. Clinical Orthopaedics & Related Research. Apr. 1983 (174):54-57.

Horowitz MC, et al. Induction of specific T-cell responsiveness to allogeneic bone. Journal of Bone & Joint Surgery—American Volume. Sep. 1991;73(8): 1157-1168.

Bobyn JD et al., Clinical validation of a structural porous tantalum biomaterial for adult reconstruction. Journal of Bone & Joint Surgery—American Volume. 2004;86-A Suppl 2:123-129.

Mardones RM, et al. Development of a biologic prosthetic composite for cartilage repair. Tissue Engineering. Sep.-Oct. 2005; 11(9-10)1368-1378.

Gordon WJ, et al., Chondroconductive potential of tantalum trabecular metal. Journal of Biomedical Research Part B, Applied Biomaterials. Nov. 2005;75(2):229-233.

Ducheyne P et al. Effect of bioactive glass templates on osteoblast proliferation and in vitro synthesis of bone-like tissue. Journal of Cellular Biochemistry. Oct. 1994;56(2):162-167.

Hench LL, et al. Bioactive glasses for in situ tissue regeneration. Journal of Biomaterials Science, Polymer Edition. 2004;15(4): 543-562.

Effah Kaufnlann EA, et al. Evaluation of osteoblast response to porous bioactive glass (4555) substrates by RT-PCR analysis. Tissue Engineering. Feb. 2000;6(1): 19-28.

el-Ghannanl A, et al. Bioactive material template for in vitro synthesis of bone. Journal of Biomedical Materials Research. Mar. 1995;29(3):359-370.

Suominen E, et al. Subchondral bone and cartilage repair with bioactive glasses, hydroxyapatite, and hydroxyapatite-glass composite. Journal of Biomedical Materials Research. Dec. 1996;32(4):543-551.

Yamashita F, et al. The transplantation of an autogeneic osteochondral fragment for osteochondritis dissecans of the knee. Clinical Orthopaedics & Related Research. Dec. 1985(201):43-50.

Lane JM, et al. Joint resurfacing in the rabbit using an autologous osteochondral graft. Journal of Bone & Joint Surgery—America Volume. Mar. 1977;59(2):218-222.

Bos GD, et al. Immune responses of rats to frozen bone allografts. Journal of Bone & Joint Surgery—American vol. Feb. 1983;65(2):239-246.

Goldberg VM, et al. Bone grafting: role of histocompatibility in transplantation. Journal of Orthopaedic Research. 1985;3(4):389-404.

Stevenson S, et al. Factors affecting bone graft incorporation. Clinical Orthopaedics and Related Research. Mar. 1996 (324):66-74.

Pylawka TK, et al. Impaction affects cell viability in osteochondral tissues during transplantation. The Journal of Knee Surgery. Apr. 2007;20(2): 105-110.

Borazjani BH, et al. Effect of impact on chondrocyte viability during insertion of human osteochondral grafts. Journal of Bone & Joint Surgery—American Volume. Sep. 2006;88(9): 1934-1943.

Marion et al., Borate glass suports the in vitro osteogenic differentiation of human mesenchymal stem cells. Mechanics of Advanced Materials & Structures. 2005; 12(3)239-246.

C.T. Hung et al., Anatomically shaped osteochondral constructs for articular cartilage repair. Journal of Biomechanics, vol. 36; 1853-1864 (2003).

* cited by examiner

SYNTHETIC OSTEOCHONDRAL COMPOSITE AND METHOD OF FABRICATION THEREOF

CROSS REFERENCE TO RELATED APPLICATION

This application claims priority from U.S. Provisional Patent Application Ser. No. 60/993,784 filed on Sep. 14, 2007 and is herein incorporated by reference in its entirety.

FIELD OF INVENTION

The present document relates to surgical apparatus and procedures, and more particularly to osteochondral composite and method of fabrication thereof.

BACKGROUND OF INVENTION

Osteochondral defects in adult knees are a common clinical finding. The limited reparative potential of such osteochondral defects has motivated numerous studies aimed at finding improved methods of treatment. Currently used procedures such as abrasion arthroplasty and microfracture, autologous chondrocyte implantation, osteochondral autografts and allografts, and partial or total joint arthroplasties have yielded varying levels of success. All current techniques suffer from deficiencies, such as donor site morbidity, limited tissue supply, immunorejection, potential transmission of pathogens, and implant loosening. Because of these issues, the development of a tissue-engineered osteochondral composite has attracted interest.

The creation of tissue-engineered osteochondral composites requires living chondrogenic cells. Commonly used cells in tissue engineering are mesenchymal stem cells (MSCs) which are multipotent progenitor cells that can undergo differentiation into other cell types, including chondrocytes. In addition, tissue-engineered osteochondral composites require synthetic substitutes for the cartilaginous extracellular matrix and subchondral support material.

The efficacy of existing tissue-engineered osteochondral composites has been hampered by the difficulty of bonding the softer material used for artificial cartilaginous extracellular matrix to the harder material used for the subchondral support material. In existing tissue-engineered osteochondral composites, the cartilaginous matrix material has been bonded to a porous ceramic or metal support material using sutures or surgical glue. To date, existing tissue-engineered osteochondral composites have had limited success due to problems associated with the separation of the artificial cartilaginous extracellular matrix from the underlying subchondral support.

Therefore, there is a need to provide a new and improved osteochondral composite and a method for fabrication thereof such that a strong and durable bond is established between the artificial cartilaginous extracellular matrix and the underlying subchondral support.

SUMMARY OF INVENTION

An osteochondral composite and method of fabrication thereof that allows homogeneous cell seeding and provides sufficient mechanical support at the same time is disclosed. In one embodiment, the osteochondral composite may include a porous supportive base with an upper surface and a lower surface. In one aspect, the osteochondral composite may include a scaffolding layer with an upper surface and a lower surface with the lower surface of the scaffolding layer being mechanically interlocked with the upper surface of the porous supportive base. In an embodiment, the scaffolding layer may incorporate biological cells implanted into a hydrogel.

In another embodiment, an osteochondral composite may include three mechanically interlocked layers: a porous base layer, a transitional layer, and a scaffolding layer. In particular, the osteochondral composite includes a porous base layer with an upper and lower surface. The lower surface of a transitional layer is bonded to the upper surface of the porous base layer. To the upper surface of the transitional layer, the lower surface of a scaffolding layer is bonded. The scaffolding layer also includes an upper surface and incorporates a hydrogel material with implanted biologic cells.

In a further embodiment, a method of fabricating an osteochondral composite is also disclosed. Specifically, a suspension of polymer and biological cells as well as a porous base with an upper and lower surface is provided. The upper surface of the porous base is submerged into the suspension to a predetermined depth. The polymers in the suspension are then crosslinked such that a hydrogel that is mechanically interlocked with the porous base is formed.

In yet another embodiment, a method of treating diseased or damaged articular cartilage in a vertebrate animal is disclosed. The method of treatment may include providing an osteochondral composite that incorporates a porous base mechanically interlocked to a hydrogel containing implanted biological cells. The osteochondral composite may be implanted within the joint of the vertebrate animal.

DETAILED DESCRIPTION OF INVENTION

Figure 1:
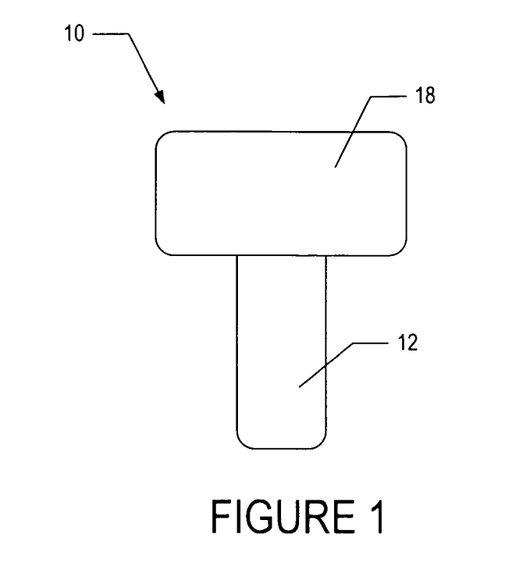
FIG. 1 illustrates a perspective view of an embodiment of the osteochondral composite.
Figure 2:
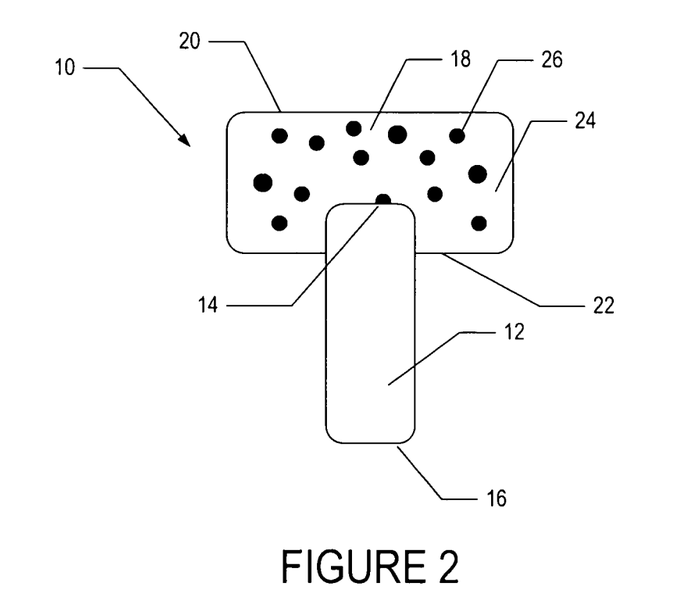
FIG. 2 illustrates a side sectional view of the osteochondral composite.

Referring to the drawings, an embodiment of an osteochondral composite is shown in FIG. 1. The osteochondral composite 10 may include a porous supportive base 12 engaged to a scaffolding layer 18. Referring to FIG. 2, the porous supportive base 12 may define an upper surface 14 and a lower surface 16, while the scaffolding layer 18 may define an upper surface 20 and a lower surface 22. In one embodiment, the lower surface 22 of the scaffolding layer 18 is mechanically interlocked to the upper surface 14 of the porous supportive base 12. In addition, the scaffolding layer 18 may further include a hydrogel 24 having a plurality of biological cells 26 implanted in the hydrogel 24.

In one embodiment, the overall diameter of the osteochondral composite 10 may range between about 0.1 mm to about 100 mm. The thickness of the scaffolding layer 18 may range between about 0.1 mm to about 5 mm. In addition, the region of overlap between the scaffolding layer 18 and the supportive base 12, in which the two layers 12 and 18 are mechanically interlocked, may range between about 0.1 mm to about 5 mm. In an embodiment, the region of overlap has a thickness ranging between about 1 mm and about 2 mm.

The thickness of the supportive base 12 depends upon the specific procedure in which the osteochondral composite 10 is to be used. However, the thickness of the supportive base 12 should be sufficient to provide adequate structural support for the scaffolding layer 18 as well as a sufficient material to interlock with the subchondral bone in which the osteochondral composite 10 is implanted. In an embodiment, the thickness may range between about 1 mm and about 100 mm.

Figure 3:
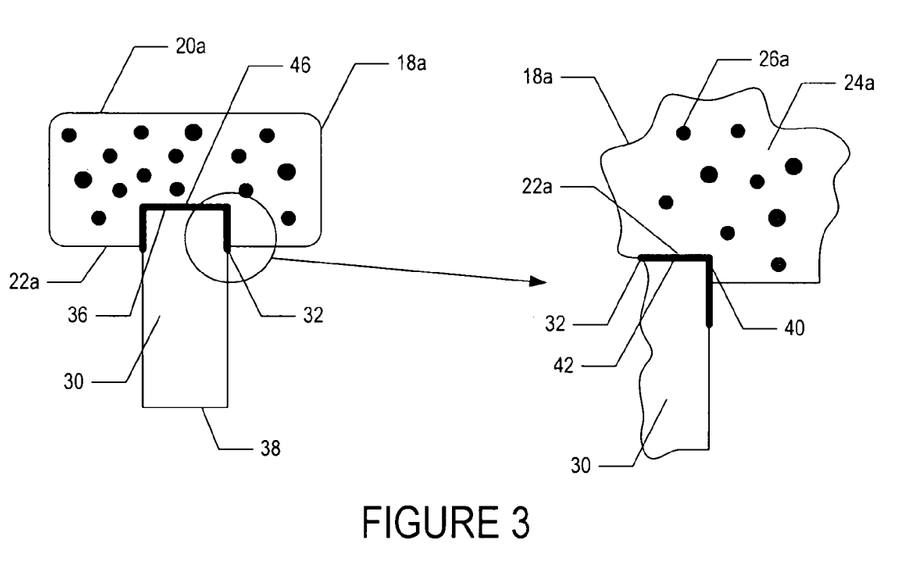
FIG. 3 illustrates a side sectional view of the osteochondral composite.

Referring to FIG. 3, another embodiment of the osteochondral composite 10 may include a porous base layer 30, a transitional layer 32, and a scaffolding layer 18a. The porous base layer 30 defines an upper surface 36 and a lower surface 38. Similarly, the transitional layer 32 may define an upper surface 40 and a lower surface 42, while the scaffolding layer may define an upper surface 20a and a lower surface 22a. The lower surface 42 of the transitional layer 32 is bonded to the upper surface 36 of the porous base layer 30, while the lower surface 46 of the scaffolding layer 34 is bonded to the upper surface 40 of the transitional layer 32. In one embodiment, the scaffolding layer 34 may further include a hydrogel 24a with a plurality of biological cells 26a implanted within the hydrogel 24a.

In an embodiment, the overall diameter of the osteochondral composite 10 may range between about 0.1 mm to about 100 mm, while the thickness of the scaffolding layer 18a may range between about 0.1 mm to about 5 mm, and the thickness of the transition layer 32 may range between about 0.1 to about 5 mm. In one embodiment, the thickness of transition layer 32 may range between about 1 mm to about 2 mm. The thickness of the porous base layer 30 may vary depending upon the specific surgical procedure. The thickness of the porous base layer 30 may range between about 1 mm to about 100 mm.

In an embodiment, the material used to construct the porous supportive base 12 and porous base layer 30 may be selected from any biocompatible porous material including allograft bone, metal, ceramic, and any combination thereof. The metal materials may be any biocompatible metal including tantalum, titanium, niobium, and combinations thereof. The ceramic material may any biocompatible ceramic including crystalline ceramic, bioactive ceramic, and combinations thereof. The bioactive ceramics may include hydroxyapatite, tricalcium phosphate, bioactive glass, bioactive glass-ceramic, and combinations thereof. The polymeric material may be any biocompatible polymer, including polycaprolactone, PCL, poly(lactic acid), PLA, poly(glycolic acid), PGA, copolymers of PLA and PGA, poly(ethylene glycol), PEG, and combinations thereof.

In another embodiment, the porous supportive base 12 and porous base layer 30 may be constructed from biocompatible materials that possess a plurality of pores on the surface that are interconnected to a network of pores in the interior of the material. The average porosity may range between about 5% to about 95% of the total volume of the material. Further, the distribution of pore sizes may be such that between about 10% to 100% of the porosity may include pores with a diameter ranging between about 10 µm to about 1000 µm. In a preferred embodiment, from about 10% to 100% of the porosity may include pores with a diameter ranging between about 200 µm to about 1000 µm.

In an embodiment, a variety of biocompatible polymers may be selected to form the hydrogel 24, including PEG (poly(ethylene glycol)), PLA (poly(lactic acid)), PGA (poly(glycolic acid)), copolymers of PLA and PGA, collagen, hyaluronan, agarose, alginate, dextran, chitosan, heparin, chiondroitan sulfate, and combinations thereof. The hydrogel 24 may be selected such that the process used to cure the hydrogel 24 is biocompatible with any biological cells 26 that may be suspended in the hydrogel 24.

In one embodiment, the biological cells 26 that are implanted into the hydrogel 24 may be living chondrogenic cells selected from the group including chondrocytes, chondroprogenitor cells, mesenchymal stem cells, mesenchymal progenitor cells, and combinations thereof. The biological cells 26 may be implanted into the hydrogel 24 at a cell density ranging between about $1 \times 10^6$ to about $100 \times 10^6$ cells/cm$^3$. In a preferred embodiment, the cell density of the biological cells 26 in the hydrogel 24 may range between about $5 \times 10^6$ to about $50 \times 10^6$ cells/cm$^3$.

In an embodiment, the hydrogel 24 may include cell culture compounds including TGF-β, DMEM low glucose medium, and fetal bovine serum. The hydrogel 24 may comprise antibiotic compounds including penicillin, streptomycin, and amphotericin in an embodiment.

Figure 4:
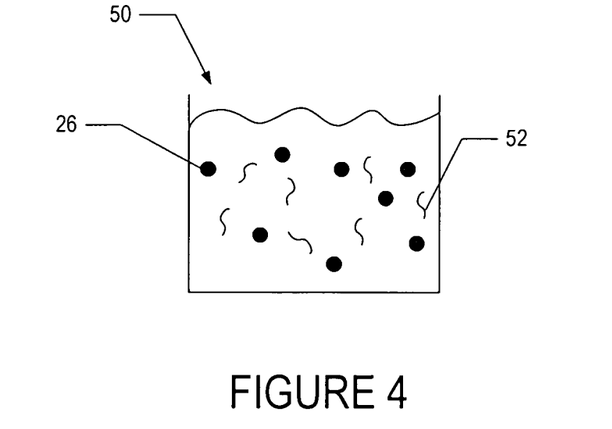
FIG. 4 illustrates the suspension of polymer and biological cells.
Figure 5:
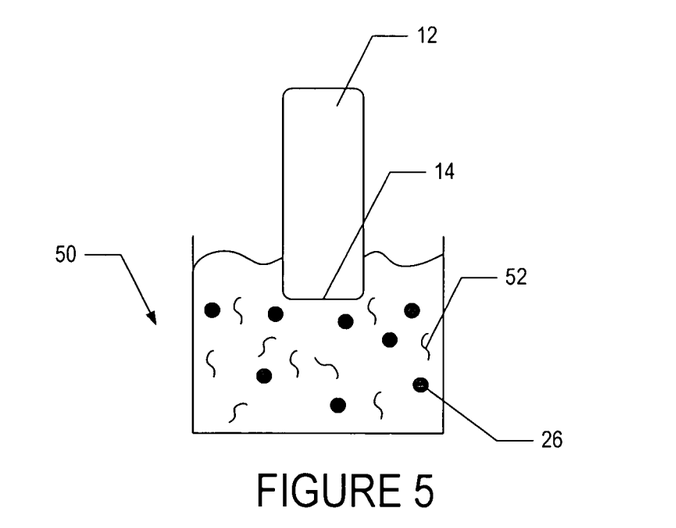
FIG. 5 illustrates the porous base submerged into the suspension of polymer and biological cells.

In one embodiment, a method for fabricating the osteochondral composite 10 may include providing a suspension 50 including a polymer 52 and a plurality of biologic cells 26, as shown in FIG. 4. The method may also include providing the porous base 12 with an upper surface 14 and a lower surface 16, and submerging the upper surface 14 of the porous base 12 into the suspension to a predetermined depth as shown in FIG. 5. Because the suspension 50 is in a liquid state, the suspension 50 may infiltrate into the pores of the porous base 12 that are submerged in the suspension 50. In an embodiment, the polymer is crosslinked such that a hydrogel 24 with the implanted biological cells 26 may be formed. In addition to the hydrogel 24 formed in the scaffolding layer 18, hydrogel 24 may also be formed inside of the pores of the porous base 12 that was submerged in the suspension 50 that is mechanically interlocked with the scaffolding layer 18.

In an embodiment, the suspension 50 may be partially crosslinked prior to submerging the porous base 12 and additional suspension 50 may then be provided after submerging the porous base 12 into the partially crosslinked suspension 50.

The suspension 50 may include a polymer 52, as described above, and biological cells 26, also described above in one embodiment. The polymer 52, in one embodiment, may further include photocrosslinkable moieties including methacrylate, methacrylate anhydride, acrylamide, propylene fumarate, and combinations thereof. The suspension may also contain biocompatible photoinitiators 54 including 2-hydroxy-2-methyl-1-phenyl-1-propanone, 2-hydroxy-1-[4-(2-hydroxyethoxy)phenyl]-2-methyl-1-propanone, and combinations thereof.

In an embodiment, the concentration of the polymer 52 in the suspension 50 may range between about 1% to about 50% by weight. In a preferred embodiment, the concentration of the polymer 52 in the suspension 50 may range between about 5% to about 20% by weight. The concentration of the biocompatible photoinitiator 54 in the suspension 50 may range between about 0.01% to about 0.1% by weight, and preferably between about 0.02% to about 0.05% by weight.

According to one embodiment, the aforementioned partially crosslinking steps or completing steps may be induced by radiation, such as ultraviolet radiation. According to another embodiment, the aforementioned crosslinking steps may also be induced by heating the solution or suspension.

In an embodiment, the ultraviolet radiation used to induce crosslinking may be applied at a wavelength ranging from about 200 nm to 500 nm and may range from about 300 nm to about 500 nm. The ultraviolet radiation may be delivered at an intensity ranging between about 2 mW/m$^2$ to about 30 mW/m$^2$, and may be between about 4 mW/m$^2$ to about 10 mW/m$^2$.

In one embodiment, a method of treating diseased or damaged articular cartilage in a vertebrate animal may comprise providing an osteochondral composite 10 comprising a porous base 12 mechanically interlocked to a hydrogel 24 having implanted biological cells 26. In addition, an embodiment of the method includes implanting the osteochondral composite 10 into a joint of a vertebrate animal. The joint may include a hip, knee, shoulder, elbow, wrist, ankle, and interphalangial joint in an embodiment. In a preferred embodiment, the vertebrate animal is a human.

EXAMPLES

To demonstrate various embodiments of the osteochondral composite, the following experiments were conducted.

Example 1

Mesenchymal Stem Cells were Obtained from Bone Marrow of NZW Rabbits

To obtain the chondrogenic cells to be incorporated into the various embodiments of the osteochondral composites discussed below, the following experiment was conducted. Bone marrow-derived mesenchymal stem cells (MSCs) were prepared from euthanized New Zealand White (NZW) rabbits, using established methods.

Marrow plugs were removed from the femur or humerus of NZW rabbits with intramedullary-pin drilling and a bone curette and then transferred to 50-ml centrifuge tubes containing 25-ml of a culture medium containing DMEM low glucose, 10% fetal bovine serum (FBS), and penicillin/streptomycin/amphotericin (p/s/a). After vortexing and spinning for 5 minutes at 1,500 rpm, the fat layer and medium were removed and the pellet was then resuspended in 8-ml of culture medium and vortexed briefly. The 8-ml suspension was drawn into a 10-ml syringe with an 18-gauge needle and transferred to a new 50-ml centrifuge tube. The needle retained small pieces of bone, and larger pieces remained in the first tube. This step was repeated twice, pooling the 8-ml samples in the new tube, and using a new needle for each aspiration.

Pooled samples were then spun for 5 minutes, supernatant fluid was removed, and the pellet was then resuspended in 10-ml of medium. A sample of the suspension was mixed with 100 μl of 4% acetic acid to disrupt the red blood cells.

The remaining cells in the suspension were plated at a density of 10$^6$ cells per T75 tissue culture plate. The medium was changed after 4 days in culture and every 3 days thereafter. Non-adhesive hematopoietic cells were discarded from the cultures while refreshing the medium.

Example 2

Bone Marrow Derived Mesenchymal Stem Cells were Cultured with Hydrogel Polymers

The bone marrow derived MSCs obtained using the methods described in Example 1 were trypsinized with 0.25% trypsin in 1 mM EDTA, counted with a hemocytometer, and then resuspended by mixing the MSCs with poly(ethylene glycol) diacrylate (PEGDA)/photoinitiator solution at a concentration of 5-10×10$^6$ cells/cm$^3$. The cell culture medium was further supplemented with 10 ng/ml TGF-β. Cell cultures were incubated for one week in 95% air/5% CO$_2$ at 37° C. with a fresh medium change every 3-4 days. After one week of culture at these conditions, chondrogenic differentiation of MSCs was achieved.

Example 3

Osteochondral Composites were Fabricated using Bioactive Glass and PEG Hydrogel

To demonstrate the feasibility of fabricating an osteochondral composite having a PEG hydrogel mechanically interlinked with a bioactive glass base, the following experiment was conducted.

In one embodiment, a bioactive glass, designated 13-93, with the composition 53 wt % SiO$_2$, 20 wt % CaO, 6 wt % Na$_2$O, 12 wt % K$_2$O, 5 wt % MgO, and 4 wt % P$_2$O$_5$ was formed into cylindrical bases. Porous 13-93 bioactive glass cylinders (3 mm diameter×3.5 mm long) were prepared by pouring glass particles ranging in size from 212-325 μm into a graphite mold, and sintered for 15 min at 700° C. to form a network of particles.

PEG hydrogel was prepared by dissolving poly(ethylene glycol)diacrylate (PEGDA) (Shearwater, Huntsville, Ala.) in sterile phosphate buffer saline (PBS) supplemented with 1% penicillin and streptomycin (Gibco, Carlsbad, Calif.) to a final solution of 10% w/v. A biocompatible ultraviolet photoinitiator, 2-hydroxy-1-[4-(hydroxyethoxy)phenyl]-2-methyl-1-propanone (Irgacure 184; Ciba, Tarrytown, N.Y.) was then added to the solution to make a final concentration of 0.05% w/v.

70 μl of hydrogel solution was added to the plastic caps of 1.5 cm$^3$ microcentrifuge tubes (Fisher Scientific, Hampton, N.H.), which had a diameter of 5 mm, resulting in a fluid height of approximately 0.5 mm inside the caps. The hydrogel solution was exposed for 4 min to a long-wave, 365 nm ultraviolet lamp (Glowmark, Upper Saddle River, N.J.) at an intensity of approximately 4 mW/cm$^2$, to partially crosslink the polymer and to increase its viscosity.

A porous glass cylinder, previously submerged in PBS for 10 min, was then placed on top of the hydrogel layer in the plastic cap, and another 50 μl of the hydrogel solution was added to the plastic cap. The glass cylinder and polymer were exposed to the same UV lamp using similar conditions for an additional 8 minutes to further crosslink the PEG hydrogel and to bind the glass to the hydrogel.

Similar osteochondral composites were fabricated using the same porous glass cylinders bound to PEG hydrogel seeded with chondrogenic cells described in Example 2 (not shown).

The results of this experiment demonstrated the feasibility of fabricating osteochondral composite comprising a hydrogel mechanically interlinked with a porous ceramic base.

Example 4

Osteochondral Composites were Fabricated using Porous Tantalum and PEG Hydrogel To demonstrate the feasibility of fabricating an osteochondral composite having a PEG hydrogel mechanically interlinked with a porous tantalum base, the following experiment was conducted. Pre-cut cylinders of porous tantalum that were 3 mm in diameter and 5 mm long were then obtained commercially (Zimmer, Warsaw, Ind.). In one embodiment, the porous tantalum cylinders were bonded to PEG hydrogel using the methods described in Example 3. Bonding of these cylinders to the MSC-loaded hydrogel was accomplished using the similar methods. The results of this experiment demonstrated the feasibility of fabricating osteochondral composites that included a hydrogel mechanically interlinked with porous tantalum, a biocompatible metal commonly used clinically for skeletal reconstruction.

Example 5

Osteochondral Composites were Fabricated using Allograft Bone and PEG Hydrogel To demonstrate the feasibility of fabricating an osteochondral composite having a PEG hydrogel mechanically interlinked with allograft bone tissue, the following experiment was conducted. Cylindrical samples of allograft tissue were prepared by removing cylinders with a diameter of 3 mm from rabbit allograft bone. The samples were processed using methods previously described for the processing of sterile human allograft bone (Musculoskeletal Transplant Foundation, Fla.).

Finally, the cylinders of allograft rabbit bone were bonded to the PEG hydrogel described in Example 3 or the MSC-seeded hydrogel described in Example 2 using the methods described in Example 3. The results of this experiment demonstrated the feasibility of fabricating osteochondral composites having a hydrogel mechanically interlinked with allograft bone tissue.

Example 6

Osteochondral Composites were Implanted into Adult NZW Rabbits using Porous Tantalum and PEG Hydrogel To assess the efficacy of implanted osteochondral composites into vertebrate joints, the following experiment was conducted. Sixty osteochondral composites were fabricated using the methods described in Example 3. The osteochondral composites were fabricated by bonding PEG hydrogel that was either seeded with mesenchymal stem cells (MSCs) or cell-free to the porous supportive bases using the methods described in Example 3.

Figure 6:
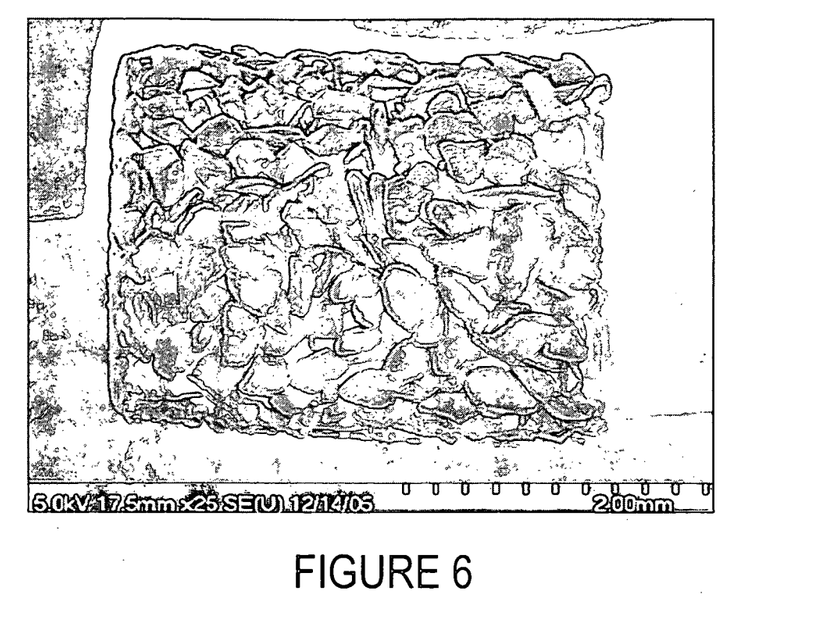
FIG. 6 is an SEM image of the 13-93 bioactive glass material according to one embodiment.
Figure 7:
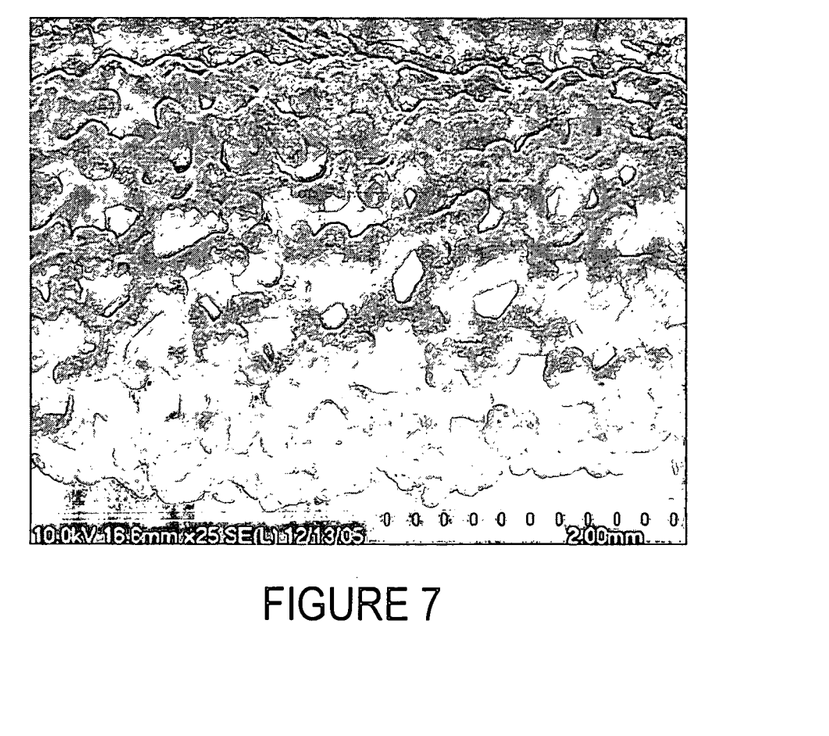
FIG. 7 is an SEM image of the trabecular tantalum material according to one embodiment.

The porous supportive bases of the osteochondral composites were fabricated from one of three materials: porous tantalum, bioactive glass, or allograft bone. Each of the three materials had differences in structure such as porosity and average pore size that could potentially influence the efficacy of the osteochondral composites that incorporated these materials. The bioactive 13-93 glass material, shown as an SEM image in FIG. 6, had a porosity of 40-45% and consisted of irregularly shaped particles and pores. The SEM image of porous tantalum metal, shown in FIG. 7 indicated that this material consisted of a cellular network with uniform pores.

Figure 8:
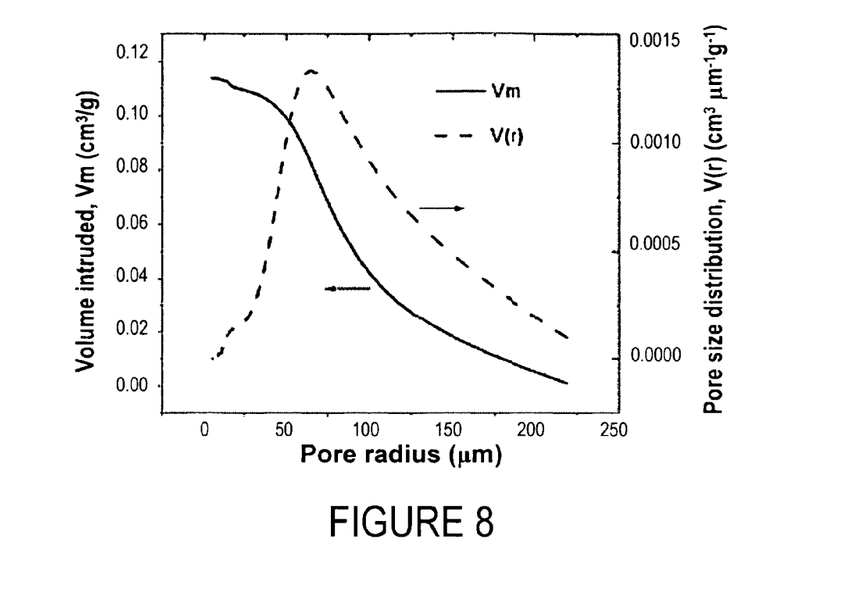
FIG. 8 is a graph summarizing the mercury porosimetry data obtained for the 13-93 bioactive glass.
Figure 9:
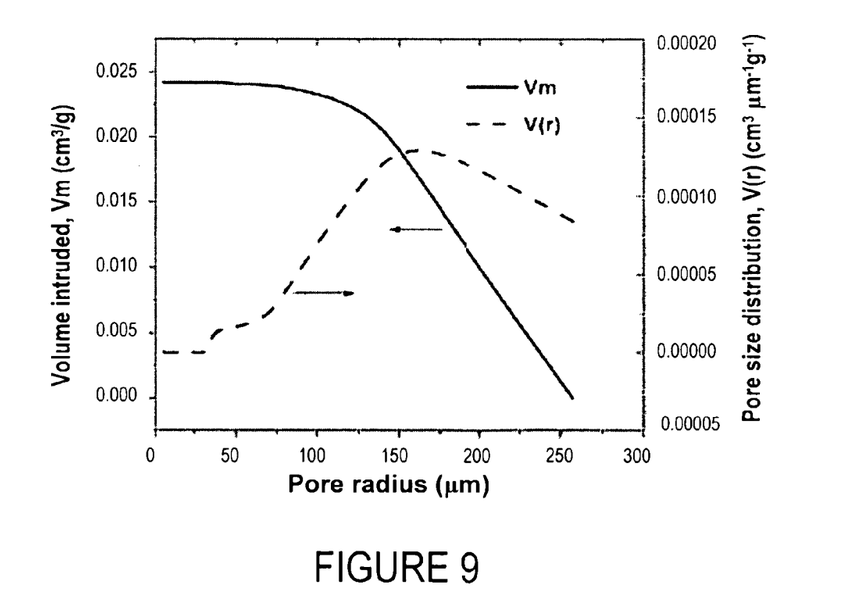
FIG. 9 is a graph summarizing the mercury porosimetry data obtained for the trabecular tantalum material.

To quantify the porosity of the two materials, mercury porosimetry data was obtained. The mercury porosimetry data obtained for the bioactive 13-93 glass material, shown in FIG. 8, indicated that approximately 80-85% of the pores in this material had a diameter of greater than 100 μm and that approximately 40% of the pores had a diameter of greater than 200 μm. However, the trabecular metal had larger pores than the bioactive glass with nearly 100% of the pores in the trabecular metal having a diameter of greater than 200 μm, as shown in FIG. 9.

Twenty adult NZW rabbits weighing more than 2 kg were premedicated, anesthetized, and prepared for aseptic surgery of one randomly chosen knee joint. Medial parapatellar arthrotomies were performed on the knee of each NZW rabbit in a single session. 3.2 mm-diameter defects were created in the articular cartilage and subchondral bone of each knee with a standard router bit. A total of four defects located in the proximal and distal trochlear region, and the proximal and distal condylar regions, respectively, were created in each knee.

The osteochondral composites were then inserted into the defects with a press fit technique, using a small forceps to push the composite surface until it was congruent with the surrounding articular surface. Treatment of the individual defects of each rabbit was randomly assigned to a combination of four different osteochondral composites. The combinations of materials used in the osteochondral composites implanted in each NZW rabbit are summarized in Table 1.

TABLE 1

| | | Knee Osteochondral Composites Implanted in NZW Rabbits | | | | | | | |
|---|---|---|---|---|---|---|---|---|---|
| | Harvest | Trochlear Groove | | | | Medial Condyle | | | |
| | Time | Proximal | | Distal | | Proximal | | Distal | |
| Rabbit | (weeks) | Base | MSC? | Base | MSC? | Base | MSC? | Base | MSC? |
| 1 | 6 | Bone | Y | Tantalum | N | Glass | Y | None | — |
| 2 | 6 | Glass | Y | Bone | Y | None | — | Tantalum | Y |
| 3 | 6 | Tantalum | Y | Glass | Y | Bone | Y | None | — |
| 4 | 6 | None | — | Tantalum | N | Glass | Y | Bone | Y |
| 5 | 6 | Bone | N | None | — | Tantalum | Y | Glass | Y |
| 6 | 6 | Glass | N | Bone | N | None | — | Tantalum | Y |
| 7 | 6 | Tantalum | N | Glass | N | Bone | N | None | — |
| 8 | 6 | Bone | Y | None | — | Glass | N | Bone | N |
| 9 | 6 | None | — | Bone | N | Tantalum | N | Glass | N |
| 10 | 6 | Glass | N | None | — | Bone | Y | Tantalum | N |
| 11 | 12 | Bone | Y | Bone | N | Tantalum | N | None | — |
| 12 | 12 | Glass | Y | Bone | Y | None | N | Tantalum | Y |

TABLE 1-continued

Knee Osteochondral Composites Implanted in NZW Rabbits

| | Harvest Time | Trochlear Groove | | | | Medial Condyle | | | |
|---|---|---|---|---|---|---|---|---|---|
| | | Proximal | | Distal | | Proximal | | Distal | |
| Rabbit | (weeks) | Base | MSC? | Base | MSC? | Base | MSC? | Base | MSC? |
| 13 | 12 | Tantalum | Y | Glass | Y | Bone | Y | None | — |
| 14 | 12 | None | — | Tantalum | Y | Glass | Y | Bone | Y |
| 15 | 12 | Bone | N | None | — | Tantalum | Y | Glass | Y |
| 16 | 12 | Glass | N | Bone | N | None | — | Tantalum | Y |
| 17 | 12 | Tantalum | Y | Glass | N | Bone | N | None | — |
| 18 | 12 | None | — | Tantalum | N | Glass | N | Bone | N |
| 19 | 12 | Glass | Y | None | — | Tantalum | N | Glass | N |
| 20 | 12 | Glass | N | Tantalum | Y | None | — | Tantalum | N |

One rabbit died intraoperatively of an apparent anesthetic complication, and was replaced. All other rabbits survived for the intended duration of study and no complications requiring treatment or alteration of the protocol were observed.

Animals were euthanized at 6 weeks (n=10) or 12 weeks (n=10) after surgery, as indicated in Table 1. At sacrifice, both knees of each rabbit were disarticulated and evaluated grossly for subjective appearance, and in addition the defect sites were stained with India ink and examined. The disarticulated knees were then processed for histologic and immunohistochemical evaluations. Matched tissues from contralateral knees served as nonoperated controls. All outcomes were scored by two investigators blinded to treatment group and time point.

The outcomes for all treatments were compared statistically to determine whether there were any significant differences in outcome due to the composition of the osteochondral composite implanted in the knees of the rabbits. All statistical analyses were performed using a computer software program (SigmaStat, Jandel Scientific, San Rafael, Calif.). Data from all samples within each group were combined and medians and means±SD were determined for each. Comparisons for statistically significant differences were made using a one-way ANOVA for continuous data. A Kruskal-Wallis one-way ANOVA on ranks was used to compare categorical data. The significance differences were defined for p values of less than 0.05.

Initial Evaluation

Figure 10:
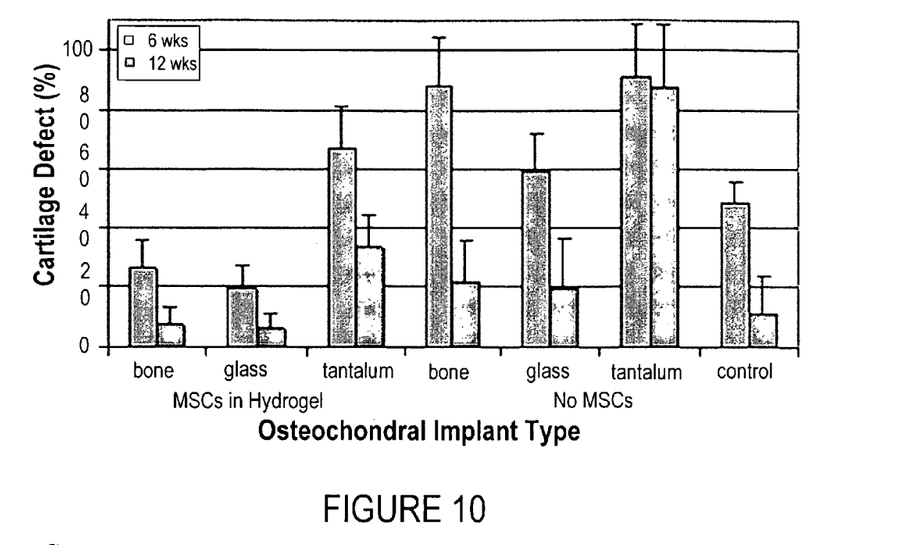
FIG. 10 shows a summary of the remaining defect sizes as determined by India ink staining for all surgical treatments.

The gross appearance of surface tissue in the surgically-created defects ranged from hyaline cartilage-like to exposed implant or bone with minimal tissue regeneration. As a gross measure of cartilage-like tissue fill for each osteochondral composite, the percentage of total surface area of each defect that stained with India ink was determined. These measurements are summarized for all osteochondral composites in FIG. 10. Six weeks after surgery, the osteochondral composites that incorporated a tantalum, bioactive glass or allograft bone base without MSCs in the hydrogel, or a tantalum base with MSCs in the hydrogel, or control (no implant) all had significantly less cartilage-like tissue than the osteochondral composites that incorporated either a bioactive glass or allograft bone base with MSCs in the hydrogel (p=0.035). At 12 weeks, the tantalum osteochondral composites with no MSCs in the hydrogel had significantly less cartilage-like tissue than any of the other groups (p=0.008). In general, significantly more cartilage-like tissue was observed after 12 weeks than after 6 weeks for all treatments (p<0.05) except for the tantalum osteochondral composite with no MSCs in the hydrogel, which showed no difference between time points.

Histologic Evaluation

Nondecalcified sections of each defect site and surrounding cartilage and bone were stained with von Kossa's and toluidine blue (University of Wisconsin). Sections were examined via light microscopy, and subjectively scored for subchondral bone restoration, defect fill, bone in-growth/implant integration, and tissue quality using the following categorical scale for each outcome measure: 0—None; 1—Poor; 2—Fair; 3—Excellent.

Figure 11:
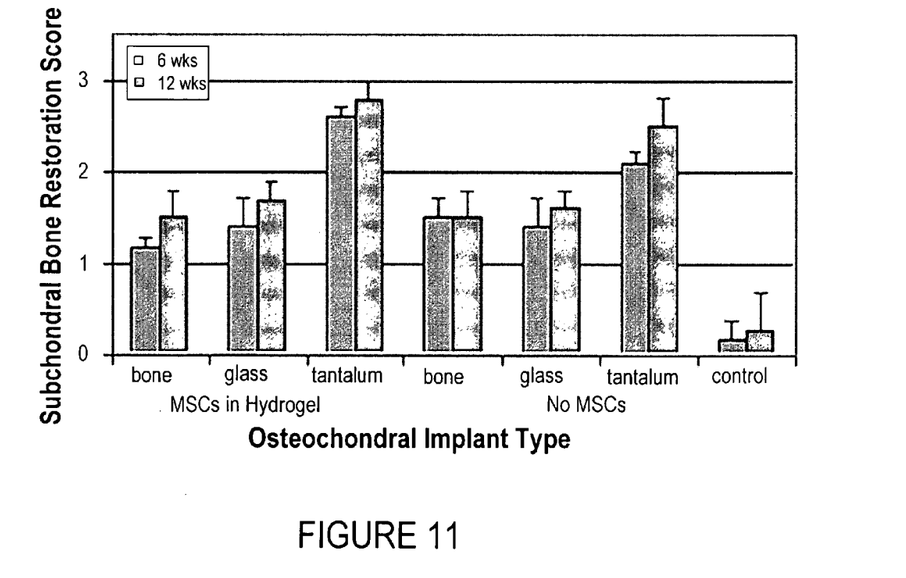
FIG. 11 shows a summary of the subchondral bone restoration scores for all surgical treatments.

At both 6 and 12 weeks, the osteochondral composites incorporating tantalum bases had significantly (p<0.05) higher subchondral bone restoration scores than all other groups (p<0.05), as shown in FIG. 11. In addition, the control treatment had significantly lower scores than all other groups (p<0.01).

Figure 12:
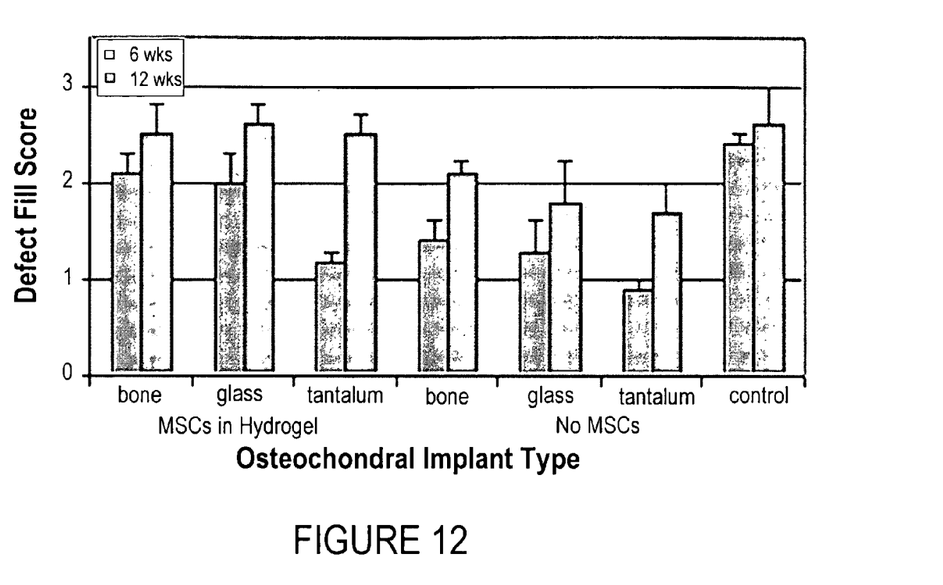
FIG. 12 shows a summary of the defect fill scores for all surgical treatments.

As shown in FIG. 12, osteochondral composites that incorporated tantalum (with and without MSCs), as well as allograft bone and bioactive glass without MSCs had significantly lower defect fill scores than all other groups (p<0.05). At 12 weeks, the tantalum osteochondral composite without MSCs was significantly lower than all other groups (p=0.045). 12-week scores were significantly higher than 6-week scores for the tanatalum osteochondral composites with and without MSCs, as well as the allograft bone without MSCs treatment (p<0.05).

Figure 13:
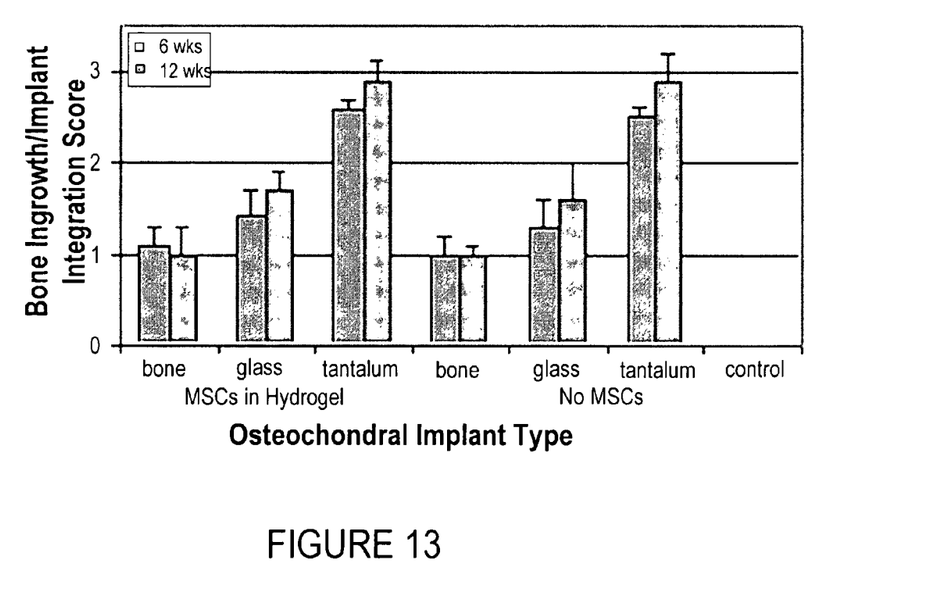
FIG. 13 shows a summary of the bone ingrowth/implant integration scores for all surgical treatments.

FIG. 13 summarizes bone in-growth/implant integration scores obtained for all treatments. At both 6 and 12 weeks, the tantalum osteochondral composites (with and without MSCs in the hydrogel) had significantly higher bone ingrowth/implant integration scores than all other groups (p<0.01).

Figure 14:
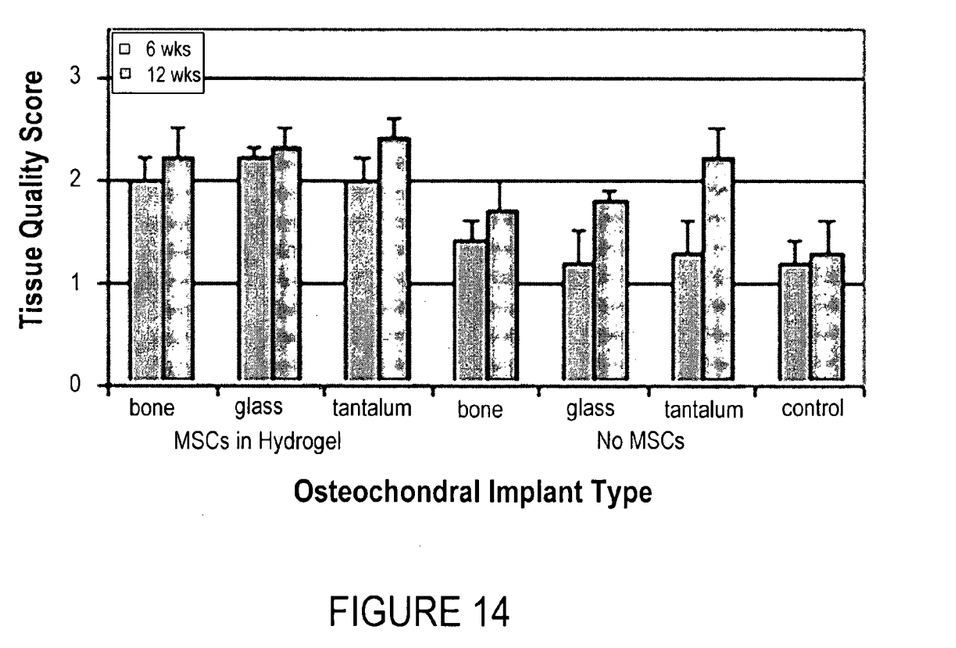
FIG. 14 shows a summary of the tissue quality scores for all surgical treatments.

At 6 weeks, all osteochondral composites with MSCs had significantly (p<0.05) higher tissue quality scores than all of the other treatments. At 12 weeks, the control treatments had significantly lower scores than all other treatments (p=0.019), as shown in FIG. 14.

Immunohistochemical Evaluation

Unstained 5 μm sections of tissue from all treatment samples were deparaffinized in xylene, rehydrated in graded ethanol solutions, and washed in 50 mM Tris buffered saline (pH 7.6)+0.15 M NaCl. Immunohistochemical staining of the collagen was performed using a purchased avidin-biotin-peroxidase kit (Vector). A serum block was used, and the primary antibody, anti-collagen type I (polyclonal Ab; Chemicon) or anti-collagen type II (polyclonal Ab; Chemicon, were applied and allowed to incubate overnight at 4° C.

The following day, the slides were incubated with biotinylated secondary antibody (DAKO). Bound primary antibody was detected using an avidin-horseradish peroxidase method with diaminobenzidine chromogenic substrate (DAKO). Positive controls (rabbit growth plate, articular cartilage, or skin) and negative controls (nonsense antibody) were included for all batches. All immunohistochemically stained sections were examined in triplicate by light microscopy by a single technician without knowledge of treatment groups of the samples. The presence and amount of positive staining for each collagen type was scored as follows: (−) if no definitive staining was observed; (+) if definitive staining was observed; and (++) if intense staining was observed. The results of the immunohiostochemical anlaysis are summarized in Table 2.

TABLE 2

Immunohistochemical Scores for Type I Collagen and Type II Collagen

| Tissue type | Time of harvest (weeks) | Osteochondral Composite | | | | | | Un-treated Control | Positive Control |
|---|---|---|---|---|---|---|---|---|---|
| | | Bone MSCs? | | Glass MSCs? | | Tantalum MSCs? | | | |
| | | Y | N | Y | N | Y | N | | |
| Type I Collagen | 6 | − | ++ | + | − | + | + | ++ | + |
| | 12 | − | + | − | − | ++ | + | ++ | + |
| Type II Collagen | 6 | − | − | ++ | − | + | + | − | ++ |
| | 12 | + | − | ++ | + | ++ | ++ | + | ++ |

− = no definitive staining;
+ = definitive staining;
++ = intense staining

The results of this experiment demonstrated that osteochondral composites could be successfully implanted into the knees of NZW rabbits as a treatment for damaged articular cartilage with good efficacy. The porous tantalum and bioactive glass materials, when used to fabricate the supportive base of the osteochondral composites, had superior integration scores into adjacent subchondral bone than allograft bone. Transplanted chondrocytes may have been lost due to the mechanical impaction of the osteochondral composites into the defects. However, the implanted osteochondral composites incorporating bioactive glass or tantalum metal demonstrated significantly greater cartilage restoration over control grafts without cells when assessed 12 weeks after implantation.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An osteochondral composite, comprising:
 a) a porous supportive base defining an upper surface and a lower surface; and,
 b) a scaffolding layer defining an upper surface and a lower surface, wherein the lower surface of the scaffolding layer is formed within a plurality of pores of the porous support base to mechanically interlock with the upper surface of the porous supportive base, and wherein the scaffolding layer includes a hydrogel having biological cells implanted therein.

2. The osteochondral composite of claim 1, wherein the porous supportive base is constructed of a biocompatible material selected from the group consisting of allograft bone, metal, ceramic, polymer, and combinations thereof.

3. The osteochondral composite of claim 2, wherein the metal is selected from the group consisting of tantalum, titanium, niobium, and combinations thereof.

4. The osteochondral composite of claim 2, wherein the ceramic is selected from the group consisting of crystalline ceramic, hydroxyapatite, tricalcium phosphate, bioactive glass, bioactive glass-ceramic, and combinations thereof.

5. The osteochondral composite of claim 2, wherein the polymeric material is selected from the group consisting of polycaprolactone, poly(lactic acid), poly(glycolic acid), copolymers of lactic acid and glycolic acid, poly(ethylene glycol), and combinations thereof.

6. The osteochondral composite of claim 1, wherein the hydrogel is selected from the group consisting of polyethylene glycol, polylactic acid, polyglycolic acid, copolymers of lactic and glycolic acid, collagen, hyaluronan, agarose, alginate, dextran, chitosan, heparin, chondroitan sulfate, and combinations thereof.

7. The osteochondral composite of claim 1, wherein the porous supportive base is a cylinder with a diameter ranging between about 1 mm to about 100 mm.

8. The osteochondral composite of claim 1, wherein the porous supportive base has a thickness ranging between about 1 mm to about 100 mm.

9. The osteochondral composite of claim 1, wherein the scaffolding layer protrudes from the upper surface of the porous supportive base with a thickness ranging between about 0.1 mm to about 5 mm.

10. The osteochondral composite of claim 1, wherein the mechanically interlocked material of the porous supportive base and scaffolding layer has a thickness ranging between about 0.1 mm to about 5 mm.

11. The osteochondral composite of claim 1, wherein the mechanically interlocked material of the porous supportive base and scaffolding layer has a thickness ranging between about 1 mm to about 2 mm.

12. The osteochondral composite of claim 1, wherein the biological cells are selected from the group consisting of chondrocytes, chondroprogenitor cells, mesenchymal stem cells, mesenchymal progenitor cells, and combinations thereof.

13. An osteochondral composite, having three mechanically interlocked layers, the layers comprising:
 a) a porous base layer defining an upper surface and a lower surface;
 b) a transitional layer defining an upper surface and a lower surface, wherein the lower surface of the transitional layer is formed within a first plurality of pores of the porous base layer to mechanically interlock with the upper surface of the porous base layer; and,
 c) a scaffolding layer defining an upper surface and a lower surface wherein the lower surface of the scaffolding layer is formed within a first plurality of pores of the porous base layer to mechanically interlock with the upper surface of the transitional layer, wherein the scaffolding layer further includes a hydrogel with implanted biologic cells.

14. The osteochondral composite of claim 13, wherein the porous base layer comprises a biocompatible material selected from the group consisting of allograft bone, metal, ceramic, polymeric material, and combinations thereof.

15. The osteochondral composite of claim 14, wherein the metal is selected from the group consisting of tantalum, titanium, niobium, and combinations thereof.

16. The osteochondral composite of claim 14, wherein the polymeric material is selected from the group consisting of polycaprolactone, poly(lactic acid), poly(glycolic acid), copolymers of lactic acid and glycolic acid, poly(ethylene glycol), and combinations thereof.

17. The osteochondral composite of claim 14, wherein the ceramic is selected from the group consisting of crystalline ceramic, hydroxyapatite, tricalcium phosphate, bioactive glass, bioactive glass-ceramic, and combinations thereof.

18. The osteochondral composite of claim 13, wherein the hydrogel is selected from the group consisting of polyethylene glycol, polylactic acid, polyglycolic acid, copolymers of lactic and glycolic acid, collagen, hyaluronan, agarose, alginate, dextran, chitosan, heparin, chondroitan sulfate, and combinations thereof.

19. The osteochondral composite of claim 13, wherein the porous base layer is a cylinder with a diameter ranging between about 1 mm to about 100 mm.

20. The osteochondral composite of claim 13, wherein the thickness of the porous base layer ranges between about 1 mm to about 100 mm.

21. The osteochondral composite of claim 13, wherein the thickness of the scaffolding layer ranges between about 0.1 mm to about 5 mm.

22. The osteochondral composite of claim 13, wherein the transitional layer has a thickness ranging between about 0.1 mm to about 5 mm.

23. The osteochondral composite of claim 13, wherein the biological cells are selected from the group consisting of chondrocytes, chondroprogenitor cells, mesenchymal stem cells, mesenchymal progenitor cells, and combinations thereof.

24. A method of fabricating an osteochondral composite comprising:
 a) providing a suspension comprising polymer and biological cells;
 b) providing a porous base defining a plurality of pores, an upper surface and a lower surface;
 c) submerging the upper surface of the porous base in the suspension to a predetermined depth; and
 d) crosslinking the polymer within the plurality of pores such that a hydrogel is formed and is mechanically interlocked with the porous base.

25. The method of claim 24, wherein the method further comprises an additional step after step b) of partially crosslinking the polymer and an additional step after step c) of providing additional aqueous suspension of polymer and biological cells.

26. The method of claim 24, wherein the polymer comprises polyethylene glycol, polylactic acid, polyglycolic acid, copolymers of lactic and glycolic acid, collagen, hyaluronan, agarose, alginate, dextran, chitosan, heparin, chondroitan sulfate, and combinations thereof.

27. The method of claim 26, wherein the polymer further comprises photocrosslinkable moieties selected from the group consisting of methacrylate, methacrylate anhydride, acrylamide, propylene fumarate, and combinations thereof.

28. The method of claim 27, wherein the suspension comprises polyethylene diacrylate at a concentration ranging between about 5% to about 20% by weight.

29. The method of claim 24, wherein the suspension comprises a biocompatible photoinitiator.

30. The method of claim 29, wherein the biocompatible photoinitiator is selected from the group consisting of 2-hydroxy-2-methyl-1-phenyl-1-propanone, 2-hydroxy-1-[4-(2-hydroxyethoxy)phenyl]-2-methyl-1-propanone, and combinations thereof.

31. The method of claim 29, wherein the suspension comprises 2-hydroxy-1-[4-(2-hydroxyethoxy)phenyl]-2-methyl-1-propanone at a concentration ranging between about 0.05% to about 0.2% by weight.

32. The method of claim 24, wherein the biological cells are selected from the group consisting of chondrocytes, chondroprogenitor cells, mesenchymal stem cells, mesenchymal progenitor cells, and combinations thereof.

33. The method of claim 24, wherein the porous base comprises a biocompatible material selected from the group consisting of allograft bone, metal, ceramic, polymer, and combinations thereof.

34. The method of claim 33, wherein the metal is selected from the group consisting of tantalum, titanium, niobium, and combinations thereof.

35. The method of claim 33, wherein the ceramic is selected from the group consisting of crystalline ceramic, hydroxyapatite, tricalcium phosphate, bioactive glass, bioactive glass-ceramic, and combinations thereof.

36. The method of claim 33, wherein the polymeric material is selected from the group consisting of polycaprolactone, poly(lactic acid), poly(glycolic acid), copolymers of lactic acid and glycolic acid, poly(ethylene glycol), and combinations thereof.

37. The method of claim 24, wherein the predetermined depth ranges between about 0.5 mm to about 5 mm.

38. The method of claim 24, wherein the crosslinking of the polymer is achieved using crosslinking methods selected from the group consisting of exposing the suspension to UV light, heating the suspension, contacting the suspension with a crosslinking catalyst compound, and combinations thereof.

39. A method of treating diseased or damaged articular cartilage in a vertebrate animal, comprising:
 a) providing an osteochondral composite comprising a porous base defining a plurality of pores mechanically interlocked to a hydrogel with implanted biological cells, wherein at least a portion of the hydrogel is formed within the plurality of pores; and,
 b) implanting the osteochondral composite into a joint of the vertebrate animal.

40. The method of claim 39, wherein the joint is selected from the group consisting of hip, knee, shoulder, elbow, wrist, ankle, and interphalangial joints.

41. The method of claim 39, wherein the vertebrate animal is a human.

* * * * *